(12) United States Patent
Oh et al.

(10) Patent No.: US 9,045,542 B2
(45) Date of Patent: Jun. 2, 2015

(54) CONTROLLING ALLERGY AND ASTHMA BY ACTIVATING HUMAN DCS VIA DECTIN-1 OR TOLL-LIKE RECEPTOR 2 (TLR2)

(75) Inventors: SangKon Oh, Baltimore, MD (US); Jacques F. Banchereau, Montclair, NJ (US); Gerard Zurawski, Midlothian, TX (US); Hideki Ueno, Plano, TX (US); Ling Ni, Dallas, TX (US)

(73) Assignee: Baylor Research Institute, Dallas, TX (US)

( * ) Notice: Subject to any disclaimer, the term of this patent is extended or adjusted under 35 U.S.C. 154(b) by 52 days.

(21) Appl. No.: 13/596,526

(22) Filed: Aug. 28, 2012

(65) Prior Publication Data

US 2013/0052193 A1 Feb. 28, 2013

Related U.S. Application Data (60) Provisional application No. 61/528,630, filed on Aug. 29, 2011.

(51) Int. Cl.

| A61K 39/00 | (2006.01) |
|---|---|
| A61K 39/395 | (2006.01) |
| C07K 16/00 | (2006.01) |
| C12P 21/08 | (2006.01) |
| C07K 16/28 | (2006.01) |
| C07K 14/33 | (2006.01) |
| C07K 14/47 | (2006.01) |
| C12N 5/0784 | (2010.01) |

(52) U.S. Cl.
CPC .............. *C07K 16/2851* (2013.01); *C07K 14/33* (2013.01); *C07K 2319/42* (2013.01); *C07K 14/4741* (2013.01); *C12N 5/0639* (2013.01)

(58) Field of Classification Search
None
See application file for complete search history.

(56) References Cited

U.S. PATENT DOCUMENTS

| 6,046,158 A * | 4/2000 | Ariizumi et al. .............. 514/21.2 |
| 2008/0233140 A1 | 9/2008 | Banchereau et al. |
| 2010/0166784 A1 | 7/2010 | Murphy et al. |

FOREIGN PATENT DOCUMENTS

| WO | WO 2008/097817 | 8/2008 |
| WO | WO 2008/118587 | 10/2008 |
| WO | WO 2011/140255 | 11/2011 |
| WO | WO 2012/021834 | 2/2012 |
| WO | WO 2012/122396 | 9/2012 |
| WO | WO 2012/061203 | 10/2012 |

OTHER PUBLICATIONS

Carter, R. et al., "Preferential Induction of CD4 T Cell Responses through in Vivo Targeting of Antigen to Dendritic Cell-Associated C-Type Lectin-1." Journal of Immunology, Volue 177, pp. 2276-2284.
Ni, L. et al., "Concomitant Activation and Antigen Uptake via Human Dectin-1 Results in Potent Antigen-specific CD8+ T Cell Responses." Journal of Immunology, vol. 185, pp. 3504-3513.
LeibundGut-Landmann, S., et al., "Syk- and CARD0-dependent Coupling of Innate Immunity to the Induction of T Helper Cells that Produce Interleukin 17." Nature Immunology, vol. 8, pp. 630-638.

\* cited by examiner

*Primary Examiner* — Nora Rooney
(74) *Attorney, Agent, or Firm* — Norton Rose Fulbright US LLP (57) ABSTRACT

The present invention includes compositions and methods for enhancing Th1/Th17 cell responses and decreasing Th2 cell responses. In various embodiments the present invention describes activation of human dendritic cells and enhancement of antigen-specific T cell responses in a Dectin-1-expressing human dendritic cells comprising an anti-Dectin-1-specific antibody or fragment thereof fused with one or more antigens. TLR2 ligands may also be included to enhance the activation and for enhancement of T-cell responses. Further, the invention also includes methods based on the compositions described herein for the treatment of allergy, and asthma.

4 Claims, 7 Drawing Sheets

CONTROLLING ALLERGY AND ASTHMA BY ACTIVATING HUMAN DCS VIA DECTIN-1 OR TOLL-LIKE RECEPTOR 2 (TLR2)

CROSS-REFERENCE TO RELATED APPLICATIONS

This application claims priority to U.S. Provisional Application Ser. No. 61/528,630, filed Aug. 29, 2011, the entire contents of which are incorporated herein by reference.

STATEMENT OF FEDERALLY FUNDED RESEARCH

This invention was made with U.S. Government support under Contract No. U19-AI057234 awarded by the National Institutes of Health (NIH). The government has certain rights in this invention.

TECHNICAL FIELD OF THE INVENTION

The present invention relates in general to allergy and asthma control, and more particularly, to delivering antigens to human dendritic cells (DCs) via Dectin-1 to enhance Th1/Th17 cell responses, decrease Th2 cell responses and to treat allergy, asthma or both by the using the enhanced Th17 cell responses.

BACKGROUND OF THE INVENTION

Without limiting the scope of the invention, its background is described in connection with targeting antigens to enhance Th1/Th17 cell responses for treatment of allergy and asthma.

U.S. Patent Application Publication No. 2010/0166784 (Murphy et al. 2010) describes a method to modulate the development of Th17 or Treg cells. The invention provides methods of modulating an immune response in a host by providing a nucleic acid sequence that modulates the development of Th17 or Treg cells.

U.S. Patent Application Publication No. 2008/0233140 (Banchereau et al. 2008) includes compositions and methods for binding Dectin-1 on immune cells with anti-Dectin-1-specific antibodies or fragment thereof capable of activating the immune cells.

SUMMARY OF THE INVENTION

The present invention describes compositions and methods for enhancing antigen-specific T cell responses in human dendritic cells. The method describes an anti-Dectin-1-specific antibody or fragment thereof fused with one or more antigens, that may be used in the presence or absence of TLR2 ligands to enhance Th1 and Th17 cell responses and at the same time decrease Th2 cell responses. Methods for treating allergy, asthma or both using the compositions described are also presented herein.

The present invention in one embodiment provides a composition for activating one or more Dectin-1-expressing antigen presenting cells (APC) to secrete IL-23 comprising: an anti-Dectin-1-specific antibody or fragment thereof fused with one or more antigens, wherein the composition enhances Th1 or Th17 cell responses and decreases Th2 cell responses. The composition as described herein is used in the treatment of an allergy, an asthma or both. The APC described in the composition herein comprises an isolated dendritic cell (DC), a peripheral blood mononuclear cell, a monocyte, a B cell, a myeloid dendritic cell or combinations thereof. In one aspect of the present invention the one or more antigens comprise bacterial, fungal or viral antigens. In another aspect the antigen is a HA1 subunit of an influenza virus. In yet another aspect the composition decreases thymic stromal lymphopoietin (TSLP) mediated OX40 ligand expression. In another aspect, the composition is adapted for administration orally, parenterally, intranasally, by inhalation, mucosally, subcutaneously, intradermally, intravenously, and intramuscularly.

The present invention also describes a method for activating one or more Dectin-1-expressing antigen presenting cells (APC) to secrete IL-23 comprising the step of contacting the APC with an anti-Dectin-1-specific antibody or fragment thereof fused with one or more antigens, wherein the composition enhances Th1 and Th17 cell responses and decreases Th2 cell responses. The method of the present invention is used in the treatment of an allergy, an asthma or both. In one aspect of the method the one or more antigens comprise bacterial, fungal or viral antigens. More specifically, the antigen is an influenza virus antigen. In another aspect the composition decreases thymic stromal lymphopoietin (TSLP) mediated OX40 ligand expression.

The present invention further provides a pharmaceutical composition for treatment of an allergy, an asthma or both comprising: an anti-Dectin-1-specific antibody or fragment thereof fused with a HA1 subunit of an influenza virus and one or more pharmaceutically acceptable excipients. The composition as described herein activates one or more Dectin-1-expressing antigen presenting cells (APC) to secrete IL-23 thereby enhancing Th1 and Th17 cell responses and decreasing Th2 cell responses. In one aspect the composition decreases thymic stromal lymphopoietin (TSLP) mediated OX40 ligand expression. In another aspect, the composition is adapted for administration orally, parenterally, intranasally, by inhalation, mucosally, subcutaneously, intradermally, intravenously, and intramuscularly.

Another embodiment of the present invention relates to a method of treating an allergy, an asthma or both in a human subject comprising the steps of: identifying the human subject in need of the treatment against the allergy, the asthma or both and administering a therapeutically effective amount of a pharmaceutical composition comprising an anti-Dectin-1-specific antibody or fragment thereof fused with an allergen and one or more pharmaceutically acceptable excipients in an amount sufficient to treat the allergy, the asthma or both. The composition disclosed in the method herein is administered orally, parenterally or intra-nasally. In another aspect, the composition is adapted for administration orally, parenterally, intranasally, by inhalation, mucosally, subcutaneously, intradermally, intravenously, and intramuscularly.

The present invention also provides a composition for activating one or more Dectin-1-expressing antigen presenting cells (APC) to secrete IL-23 comprising: an anti-Dectin-1-specific antibody or fragment thereof fused with one or more antigens and one or more TLR2 ligands, wherein the composition enhances Th1 and Th17 cell responses and decreases Th2 cell responses. In one aspect the composition is used in the treatment of an allergy, an asthma or both. In another aspect the APC comprises an isolated dendritic cell (DC), a peripheral blood mononuclear cell, a monocyte, a B cell, a myeloid dendritic cell or combinations thereof. Inn yet another aspect the one or more antigens comprise an allergen selected from a bacterial, a fungal or a viral antigen. In another aspect the one or more TLR2 ligands comprise heat-killed bacteria, lipoglycans, lipopolysaccharide, lipoteichoic acids, peptidoglycans, synthetic lipoproteins, zymosan or combinations and modifications thereof. In a specific aspect the composition comprises lipopolysaccharides comprising

*P. gingivalis* LPS or *E. coli* LPS or both and the composition decreases thymic stromal lymphopoietin (TSLP) mediated OX40 ligand expression. In another aspect, the composition is adapted for administration orally, parenterally, intranasally, by inhalation, mucosally, subcutaneously, intradermally, intravenously, and intramuscularly.

The present invention further provides a method for activating one or more Dectin-1-expressing antigen presenting cells (APC) to secrete IL-23 comprising the step of: contacting the APC with an amount of an anti-Dectin-1-specific antibody or fragment thereof fused with one or more antigens and one or more TLR2 ligands, wherein the composition enhances Th1 and Th17 cell responses and decreases Th2 cell responses. In another aspect, the composition is adapted for administration orally, parenterally, intranasally, by inhalation, mucosally, subcutaneously, intradermally, intravenously, and intramuscularly.

In yet another embodiment the present invention describes a pharmaceutical composition for treatment of an allergy, an asthma or both comprising: (i) an anti-Dectin-1-specific antibody or fragment thereof fused with a HA1 subunit of an influenza virus, (ii) one or more TLR2 ligands comprising *P. gingivalis* LPS or *E. coli* LPS or both; and (iii) one or more optional pharmaceutically acceptable excipients. In one aspect the composition activates one or more Dectin-1-expressing antigen presenting cells (APC) to secrete IL-23 thereby enhancing Th1 and Th17 cell responses and decreasing Th2 cell responses. In another aspect the composition decreases thymic stromal lymphopoietin (TSLP) mediated OX40 ligand expression. In another aspect, the composition is adapted for administration orally, parenterally, intranasally, by inhalation, mucosally, subcutaneously, intradermally, intravenously, and intramuscularly.

The present invention also provides a method of treating an allergy, an asthma or both in a human subject comprising the steps of: identifying the human subject in need of the treatment against the allergy, the asthma or both and administering a therapeutically effective amount of a pharmaceutical composition comprising an anti-Dectin-1-specific antibody or fragment thereof fused with a viral antigen and one or more pharmaceutically acceptable excipients in an amount sufficient to treat the allergy, the asthma or both. In another aspect, the composition is adapted for administration orally, parenterally, intranasally, by inhalation, mucosally, subcutaneously, intradermally, intravenously, and intramuscularly.

BRIEF DESCRIPTION OF THE DRAWINGS

For a more complete understanding of the features and advantages of the present invention, reference is now made to the detailed description of the invention along with the accompanying figures and in which:

(FIG. 1A) shows that human DCs loaded with anti-hDectin-1-HA1 secrete IL-23, (FIG. 1B) shows that blocking IL-23 resulted in decreased Th1 and Th17, but enhanced Th2 cell responses;

FIGS. 4A and 4B show that OX40L expressed on human DCs is a key factor for the enhancement of Th2 cell responses. FIG. 4A shows that blocking OX40L with anti-OX40L antibody resulted in decreased HA-specific Th2 cell responses, the data in FIG. 4B is consistent with the data in FIG. 4A;

DETAILED DESCRIPTION OF THE INVENTION

Figure 1A:
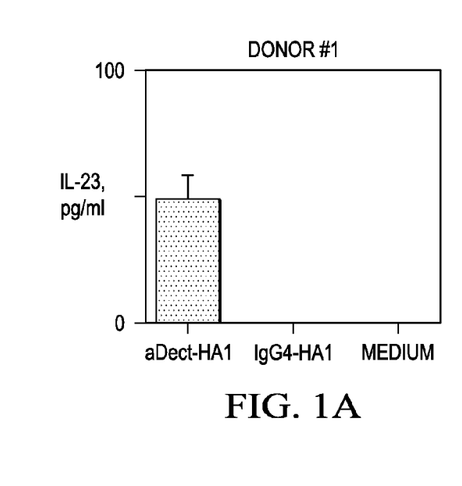
FIGS. 1A and 1B shows that anti-hDectin-1-HA1 fusion proteins activate DCs to secrete IL-23 that contributes to the enhanced Th1 and Th17, but decreased Th2 cell responses.
Figure 1B:
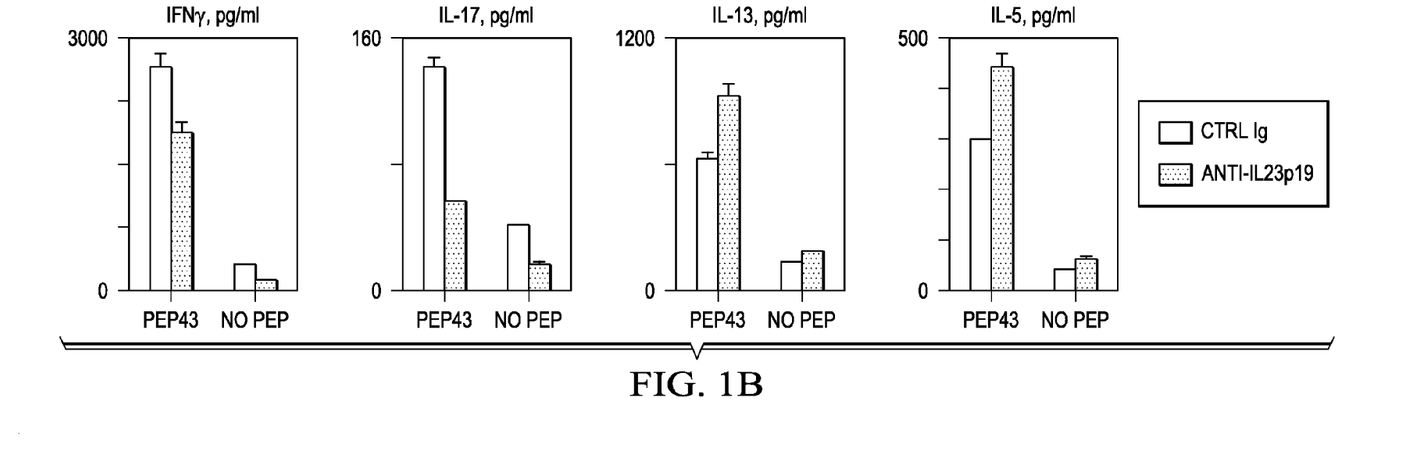
Figure 2:
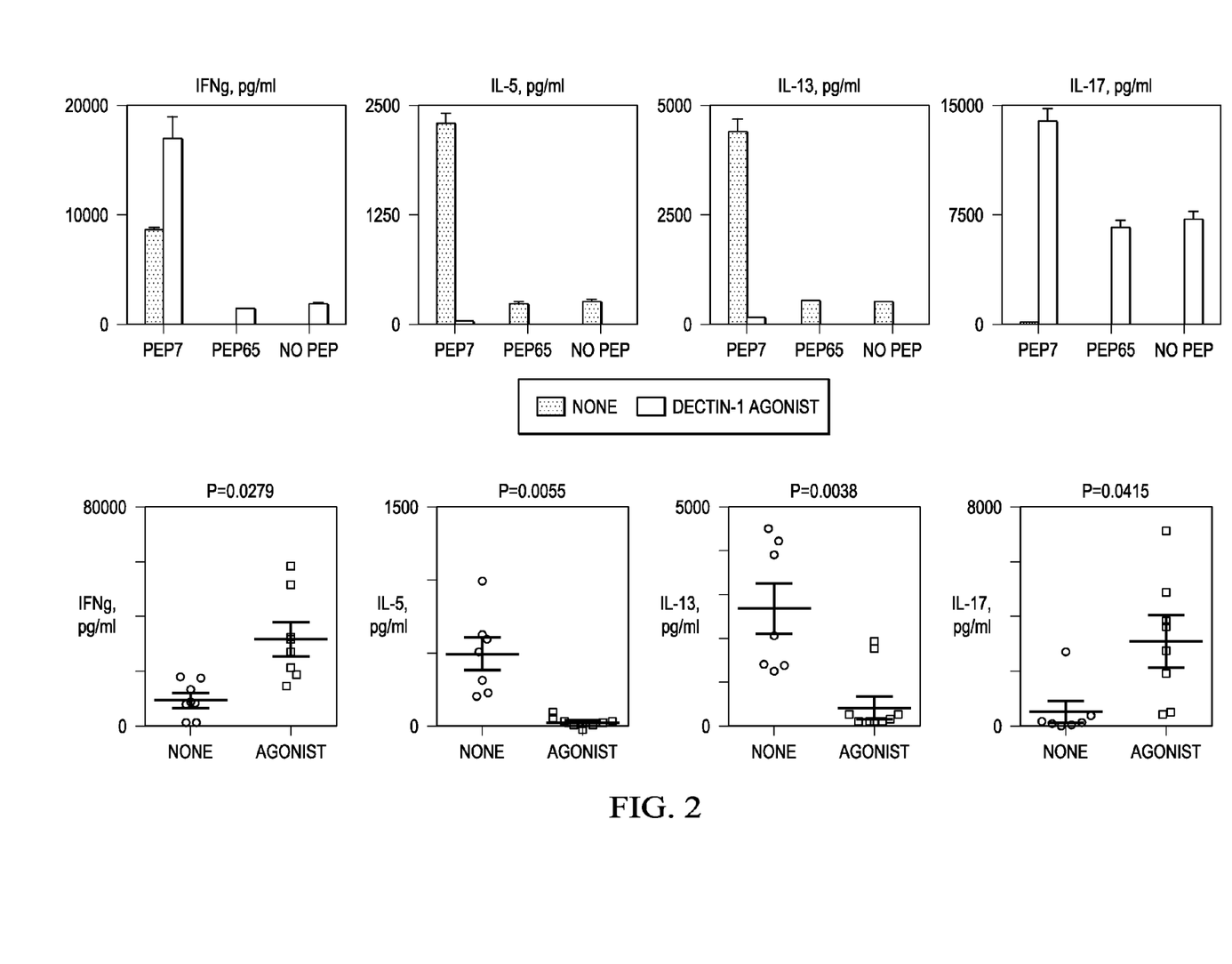
FIG. 2 shows human DCs activated with Dectin-1 agonists result in enhanced antigen-specific Th1/Th17, but decreased Th2 cell responses. The lower panel summarizes the data from 7 independent runs using cells from different healthy donors.
Figure 3:
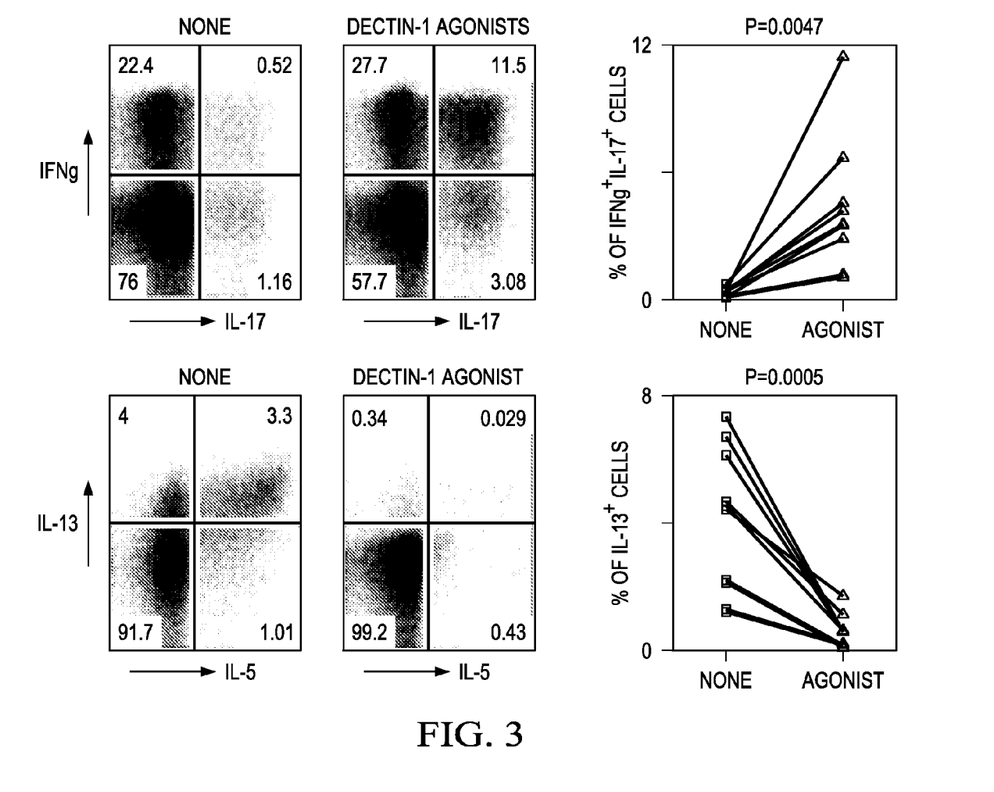
FIG. 3 shows human DCs activated with Dectin-1 agonists result in enhanced total Th1/Th17, but decreased Th2 cell responses. The right two panels in FIG. 3 are the summary of data from 9 independent runs using cells from different healthy donors.
Figure 4A:
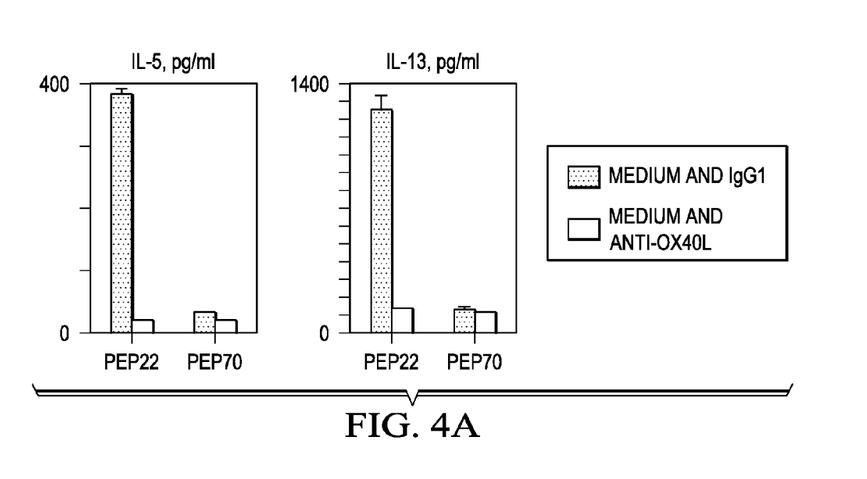
Figure 4B:
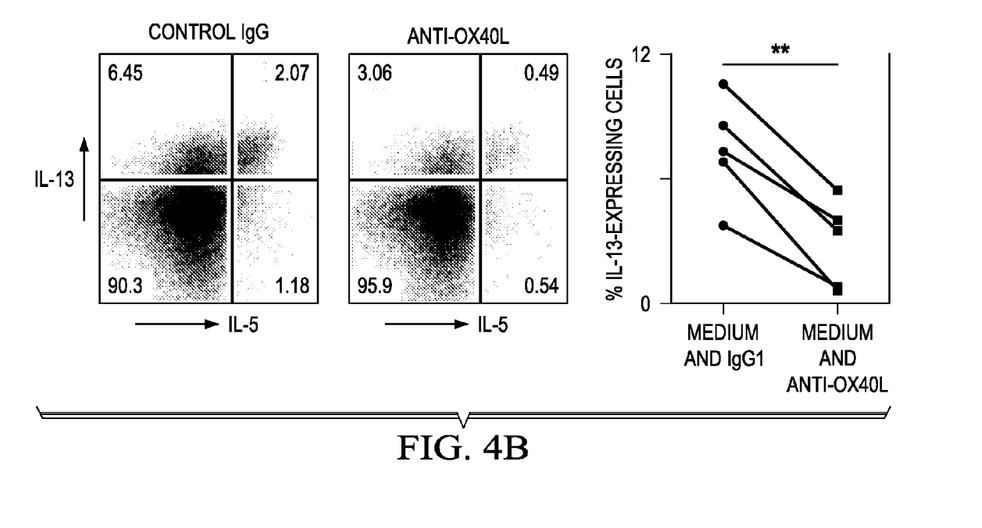
Figure 5:
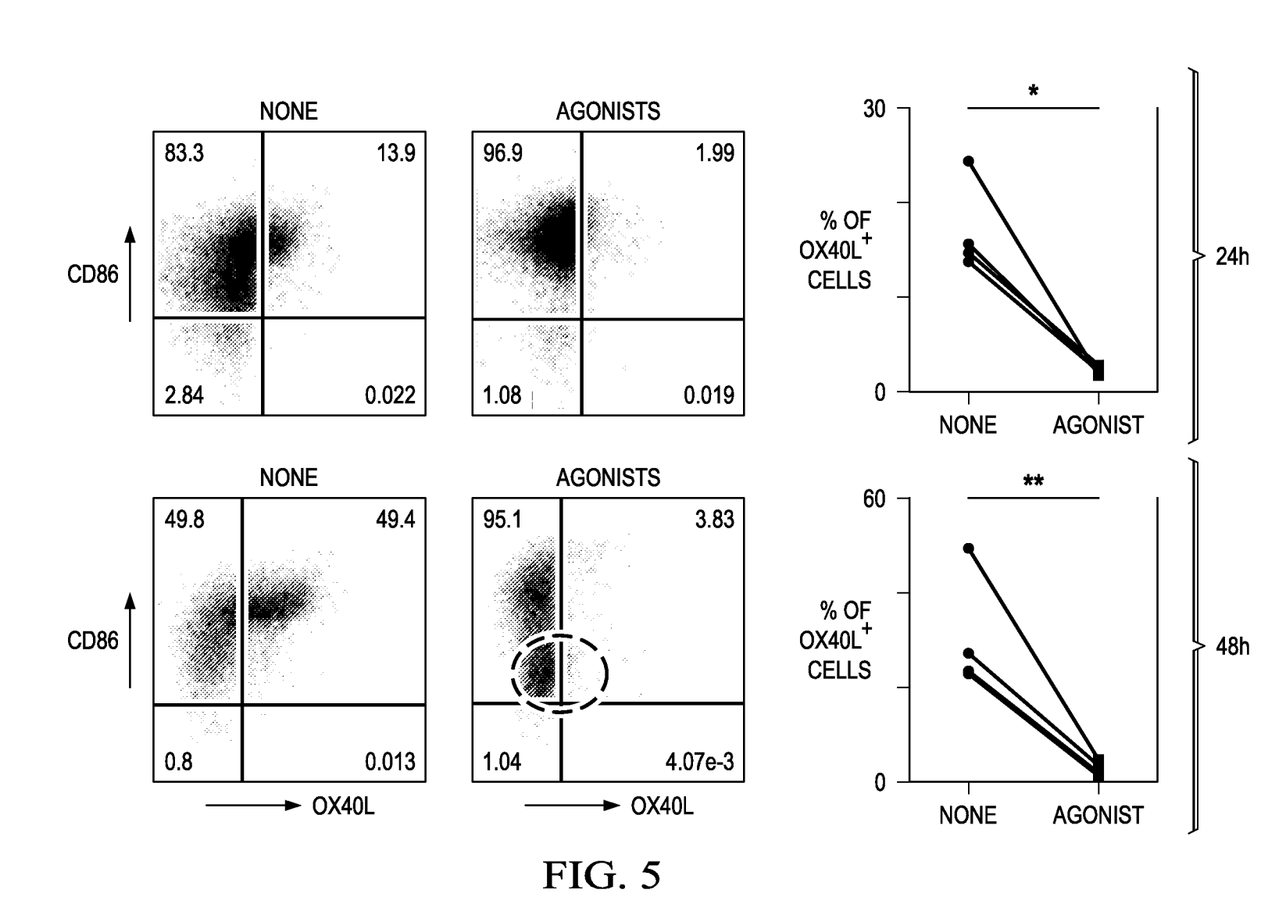
FIG. 5 shows Dectin-1 agonists down regulate OX40L expression on human Dcs: DCs express OX40L on their surface after 24 h (upper panels in FIG. 5) and 48 h incubation (lower panels in FIG. 5). At both time points, Dectin-1 agonists down regulate the surface expression of OX40L.
Figure 6:
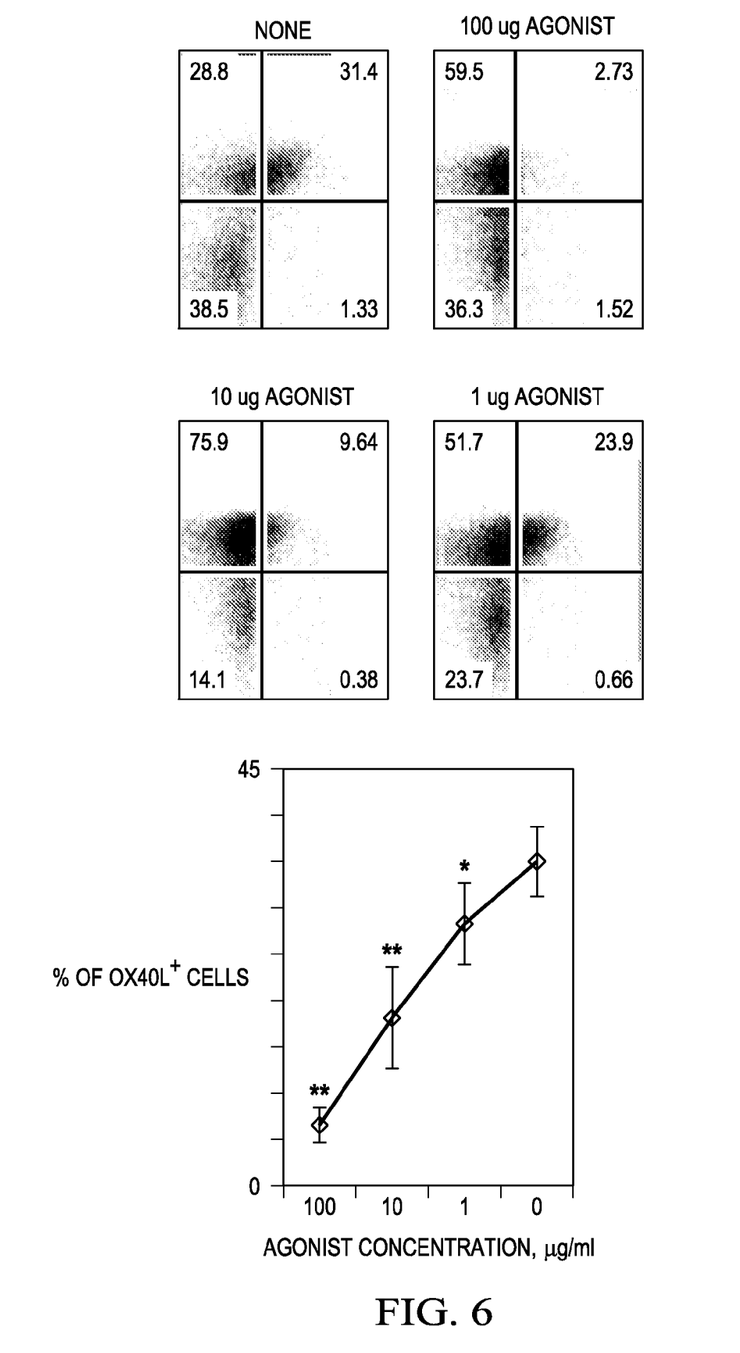
FIG. 6 shows the down regulation of OX40L expression on TSLP-activated blood mDCs by Dectin-1 agonists.
Figure 7:
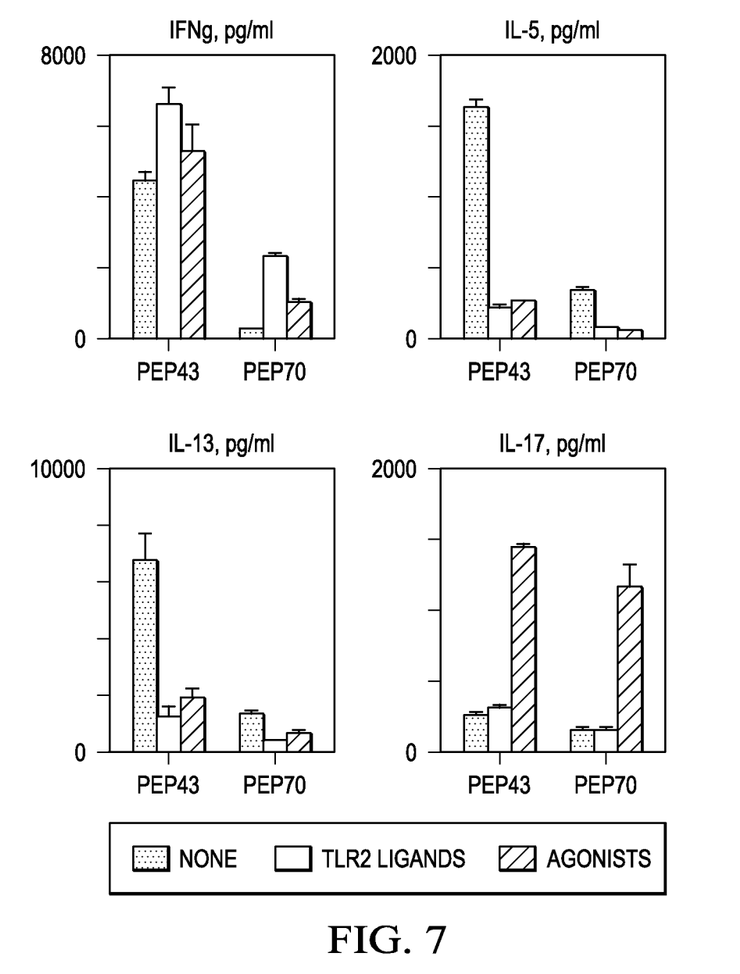
FIG. 7 shows Dectin-1 agonists and TLR2 ligands abrogating the antigen-specific Th2 cell responses elicited by TSLP-activated DCs.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an," and "the" are not intended to refer to only a singular entity, but include the general class of which a specific example may be used for illustration. The terminology herein is used to describe specific embodiments of the invention, but their usage does not delimit the invention, except as outlined in the claims.

As used herein, the term "Antigen Presenting Cells" (APC) refers to cells that are capable of activating T cells, and include, but are not limited to, certain macrophages, B cells and dendritic cells. "Dendritic cells" (DCs) refers to any member of a diverse population of morphologically similar cell types found in lymphoid or non-lymphoid tissues. These cells are characterized by their distinctive morphology, high levels of surface MHC-class II expression (Steinman, et al. Ann. Rev. Immunol. 9:271 (1991); incorporated herein by reference for its description of such cells). These cells can be isolated from a number of tissue sources, and conveniently, from peripheral blood, as described herein. Dendritic cell binding proteins refers to any protein for which receptors are expressed on a dendritic cell. Examples include GM-CSF, IL-1, TNF, IL-4, CD40L, CTLA4, CD28, and FLT-3 ligand.

For the purpose of the present invention, the term "vaccine composition" is intended to mean a composition which can be administered to humans or to animals in order to induce an immune system response; this immune system response can result in a production of antibodies or simply in the activation of certain cells, in particular antigen-presenting cells, T lymphocytes and B lymphocytes. The vaccine composition can be a composition for prophylactic purposes or for therapeutic purposes, or both. As used herein, the term "antigen" refers to any antigen which can be used in a vaccine, whether it involves a whole microorganism or a subunit, and whatever its nature: peptide, protein, glycoprotein, polysaccharide, glycolipid, lipopeptide, etc. They may be viral antigens, bacterial antigens, or the like; the term "antigen" also comprises the polynucleotides, the sequences of which are chosen so as to encode the antigens whose expression by the individuals to which the polynucleotides are administered is desired, in the case of the immunization technique referred to as DNA immunization. They may also be a set of antigens, in particular in the case of a multivalent vaccine composition which comprises antigens capable of protecting against several diseases, and which is then generally referred to as a vaccine combination, or in the case of a composition which comprises several different antigens in order to protect against a single disease, as is the case for certain vaccines against whooping cough or the flu, for example. The term "antibodies" refers to immunoglobulins, whether natural or partially or wholly produced artificially, e.g. recombinant. An antibody may be monoclonal or polyclonal. The antibody may, in some cases, be a member of one, or a combination immunoglobulin classes, including: IgG, IgM, IgA, IgD, and IgE. In one example, the composition is adapted for administration orally, parenterally, intranasally, by inhalation, mucosally, subcutaneously, intradermally, intravenously, and intramuscularly.

The term "adjuvant" refers to a substance that enhances, augments or potentiates the host's immune response to a vaccine antigen.

The term "gene" is used to refer to a functional protein, polypeptide or peptide-encoding unit. As will be understood by those in the art, this functional term includes both genomic sequences, cDNA sequences, or fragments or combinations thereof, as well as gene products, including those that may have been altered by the hand of man. Purified genes, nucleic acids, protein and the like are used to refer to these entities when identified and separated from at least one contaminating nucleic acid or protein with which it is ordinarily associated.

As used herein, the term "nucleic acid" or "nucleic acid molecule" refers to polynucleotides, such as deoxyribonucleic acid (DNA) or ribonucleic acid (RNA), oligonucleotides, fragments generated by the polymerase chain reaction (PCR), and fragments generated by any of ligation, scission, endonuclease action, and exonuclease action. Nucleic acid molecules can be composed of monomers that are naturally-occurring nucleotides (such as DNA and RNA), or analogs of naturally-occurring nucleotides (e.g., α-enantiomeric forms of naturally-occurring nucleotides), or a combination of both. Modified nucleotides can have alterations in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, and the like. The term "nucleic acid molecule" also includes so-called "peptide nucleic acids," which comprise naturally-occurring or modified nucleic acid bases attached to a polyamide backbone. Nucleic acids can be either single stranded or double stranded.

As used in this application, the term "amino acid" means one of the naturally occurring amino carboxylic acids of which proteins are comprised. The term "polypeptide" as described herein refers to a polymer of amino acid residues joined by peptide bonds, whether produced naturally or synthetically. Polypeptides of less than about 10 amino acid residues are commonly referred to as "peptides." A "protein" is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell. Proteins are defined herein in terms of their amino acid backbone structures; substituents such as carbohydrate groups are generally not specified, but may be present nonetheless.

As used herein, the term "in vivo" refers to being inside the body. The term "in vitro" used as used in the present application is to be understood as indicating an operation carried out in a non-living system.

As used herein, the term "treatment" or "treating" means any administration of a compound of the present invention and includes (1) inhibiting the disease in an animal that is experiencing or displaying the pathology or symptomatology of the diseased (i.e., arresting further development of the pathology and/or symptomatology), or (2) ameliorating the disease in an animal that is experiencing or displaying the pathology or symptomatology of the diseased (i.e., reversing the pathology and/or symptomatology).

The instant invention describes methods and compositions for enhancing Th1/Th17 cell responses and decreasing Th2 cell responses by targeting antigens to human dendritic cells (DCs) via Dectin-1. The present invention further provides a strategy for controlling allergy and asthma by activating human DCs via Dectin-1 or toll-like receptor 2.

Asthma and atopic dermatitis (AD) are inflammatory disorders characterized by the infiltration and accumulation of memory-like Th2 cells and eosinophils. In addition to the type 2 inflammatory processes, allergic diseases often involve epithelial cell stress and injury. This results in the release of chemokines and growth factors that are able to support both chronic inflammatory and remodeling responses.

Reduced barrier function of the epithelium and altered innate immunity are fundamental to the origin of these diseases. This foundation is supported by the recent finding that thymic stromal lymphopoietin (TSLP), an IL-7-like cytokine, plays a key role in allergic inflammation at the interface between epithelial cells and DCs. TSLP is highly expressed by keratinocytes in skin lesions of patients with AD and by airway epithelial cells of individuals with asthma. TSLP can potently activate myeloid DCs by upregulating their surface expression of MHC class II, CD54, CD80, CD83, CD86, and DC-lamp.

Interestingly, TSLP triggers human myeloid DCs to produce a myriad of chemokines that recruit eosinophils and Th2 cells; however, it does not trigger the production of either Th1-polarizing cytokines of the IL-12 family or the proinflammatory cytokines TNF-α, IL-1β, and IL-6; resulting in a microenvironment permissive for type 2 inflammatory responses. TSLP activated DCs can induce naive T cells to differentiate into inflammatory Th2 cells; producing the classical Th2 cytokines IL-4, IL-5, and IL-13, a large amount of TNF-α, but little or no IL-10. Moreover, only TSLP-activated DCs can induce in vitro, allergen-specific Th2 memory cells to undergo homeostatic expansion, further Th2 polarization, and mediate recall responses. In support of the findings in humans, mice with conditional over expression of TSLP in keratinocytes were found to have an AD-like phenotype. This phenotype is characterized by scaling lesions accompanied by infiltration of Th2 CD4+ cells in skin and elevated serum IgE level.

Studies have shown that many of the DC surface receptors have unique function in activating DCs which can result in a different quantity and quality of immune responses. In particular, DCs express multiple pattern-recognition receptors, including toll-like receptors and lectin-like receptors. Of those surface receptors, we have recently found that Dectin-1 and TLR2 expressed on DCs have unique function in inhibiting Th2 type CD4+ T cell responses.

The present inventors have developed an agonistic anti-human Dectin-1 monoclonal antibody that could activate human DCs. Recombinant fusion proteins of anti-hDectin-1 and influenza viral HA1 were generated.

Cells:

Peripheral blood mononuclear cells (PBMCs) of healthy volunteers were fractionated by elutriation, according to Institutional Review Board guidelines. IL-4DCs and IFNDCs were generated by culturing monocytes from healthy donor in serum free media (Cellgenix, Germany) supplemented with GM-CSF (100 ng/ml) and IFNα (500 units/ml) (IFNDCs) or GM-CSF (100 ng/ml) and IL-4 (50 ng/ml). The medium was replenished with cytokines on day 1 for IFNDCs and on day 3 for IL-4DCs. IFNα, IL-4 and GM-CSF were from the Pharmacy in Baylor University Medical Center (Dallas, Tex.). Autologous CD4+ T cells were purified using EasySep Human CD4+ T Cell Enrichment Kit (Stemcell, CA). Monocytes and B cells from PBMCs were purified with enrichment kits (StemCell, CA). Naïve (CD45RA+CD45RO−) and memory CD4+ T cells (CD45RA-CD45RO+) (purity>99.2%) were purified by FACS Aria (BD Biosciences).

Peptides:

Overlapping (staggered by 11 amino acids) 17-mer peptides spanning the entire HA1 subunit of HA (A/PR/8/34 H1N1) were synthesized by Biosynthesis (TX).

Expression and purification of chimeric recombinant mAbs fused to HA1: Total RNA was prepared from hybridoma cells using RNeasy kit (Qiagen, CA) and used for cDNA synthesis and PCR (SMART RACE kit, BD Biosciences). PCR products were then cloned (pCR2.1 TA kit, Invitrogen) and characterized by DNA sequencing (MC Lab, CA). Using the derived sequences for the mouse heavy (H) and light (L) chain variable (V)-region cDNAs, specific primers were used to PCR amplify the signal peptide and V-regions while incorporating flanking restriction sites for cloning into expression vectors encoding downstream human IgG4H regions. The vector for expression of chimeric mVκ-hIgκ was built by amplifying residues 401-731 (gi|63101937|) flanked by Xho I and Not I sites and inserting this into the Xho I—Not I interval of pIRES2-DsRed2 (BD Biosciences). PCR was used to amplify the mAb Vk region from the initiator codon, appending a Nhe I or Spe I site then CACC, to the region encoding (e.g., residue 126 of gi|76779294|), appending a distal Xho I site. The PCR fragment was then cloned into the Nhe I—Not I interval of the above vector. The control human IgGκ sequence corresponds to gi|49257887| residues 26-85 and gi|21669402| residues 67-709. The control human IgG4H vector corresponds to residues 12-1473 of gi|19684072| with S229P and L236E substitutions, which stabilize a disulphide bond and abrogate residual FcR interaction (30), inserted between the Bgl II and Not I sites of pIRES2-DsRed2 while adding the sequence 5' gctagctgattaattaa 3' instead of the stop codon. PCR was used to amplify the mAb VH region from the initiator codon, appending CACC then a Bgl II site, to the region encoding residue 473 of gi|19684072|. The PCR fragment was then cloned into the Bgl II-Apa I interval of the above vector.

The Flu HA1 antigen coding sequence is a CipA protein [*Clostridium. thermocellum*] gi|479126| residues 147-160 preceding hemagglutinin [Influenza A virus (A/Puerto Rico/8/34(H1N1))] gi|126599271| residues 18-331 with a P321L change and with 6 C-terminal His residues was inserted between the H chain vector Nhe I and Not I sites to encode recombinant antibody-HA1 fusion proteins. Stable CHO-S cells were grown in GlutaMAX and HT media (Invitrogen) and recombinant proteins were purified by protein A column chromatography. Purified proteins were confirmed by reduced-SDS gel analysis.

Binding of recombinant fusion proteins to hDectin-1 and APCs: $2\times10^5$ cells (293F cells transfected with full length of hDectin-1 and IFNDCs) were incubated with different concentrations of recombinant fusion proteins (anti-hDectin-1-HA1 and IgG4-HA1) for 20 min at 4° C. Cells were then washed twice with 2% FCS in PBS, and then stained with secondary antibody, anti-human IgG-PE, for 20 min. Cells were analyzed by flow cytometry.

RT-PCR: Total RNA was isolated from cell lysates using QIAGEN RNeasy "Mini" spin columns according to the instructions of the manufacturer and then subjected to a 20 mL cDNA synthesis reaction (Promega). Random primers were used as primer. 2.5 mL cDNA was used for PCR amplification. The primer sequences and PCR temperature profiles for T-bet, RORC, GATA-3, and b-actin is provided in Table 1. A total of 4 µL of the reverse transcriptase (RT)-PCR reactions was electrophoresed through a 4-12% Bis-Tris gel and stained with ethidium bromide for visualization under ultraviolet light.

TABLE 1

Primer sequences and PCR temperature profiles.

| Primer | Sequence | PCR Temperature Profile |
|---|---|---|
| T-bet | T-bet forward: (SEQ ID NO: 1) CACTACAGGATGTTTGTGGACGTG T-bet reverse: (SEQ ID NO: 2) CCCCTTGTTGTTTGTGAGCTTTAG | 1. 5 minutes of pretreatment at 94° C. 2. 30 cycles at 94° C. for 15 seconds 3. 55° C. for 30 seconds 4. 72° C. for 1 minute |
| RORC | RORc forward: (SEQ ID NO: 3) TCTGGAGCTGGCCTTTCATCATCA RORc reverse: (SEQ ID NO: 4) TCTGCTCACTTCCAAAGAGCTGGT | |
| GATA-3 | GATA-3 forward: (SEQ ID NO: 5) AACTGTGGGGCAACCTCGAC GATA-3 reverse: (SEQ ID NO: 6) TTGCAGACAGGGTCCCCATT | |

TABLE 1 -continued

Primer sequences and PCR temperature profiles.

| Primer | Sequence | PCR Temperature Profile |
|---|---|---|
| ACTB | ACTB forward: (SEQ ID NO: 7)<br>GGATGCAGAAGGAGATCACT<br>ACTB reverse: (SEQ ID NO: 8)<br>CGATCCACACGGAGTACTTG | |

Statistical Analysis: Statistical significance was determined using the Student's t-test and significance was set at P<0.05. Spearman's correlations statistics were used.

Anti-hDectin-1-HA1 can target hDectin-1 molecules expressed on DCs: To target HA1 to DCs via hDectin-1, recombinant proteins of an agonistic anti-hDectin-1 mAb (Ni et al. 2010) fused to HA1 subunit of influenza viral hemagglutinin (A/PR8/34, H1N1) (anti-hDectin-1-HA1) were generated and analyzed in reduced SDS-gel. A human $IgG_4$-HA1 fusion protein was made as a control. Anti-hDectin-1 mAb was engineered as a chimera containing mouse V-region and human IgG4 Fc with two site mutations to abrogate residual non-specific binding capacity to Fc receptors (30).

FIG. 1A shows that human DCs loaded with anti-hDectin-1-HA1 secrete IL-23. To test the role of IL-23 in the modulation of the quality of antigen-specific CD4+ T cell responses, purified autologous CD4+ T cells were co-cultured with DCs loaded with anti-hDectin-1-HA1 in the presence of anti-IL-23 or control antibodies by the present inventors. On day 7, CD4+ T cells were restimulated with HA1-derived peptides for 36 h. Cytokines in culture supernatants were measured. FIG. 1B shows that blocking IL-23 resulted in decreased Th1 and Th17, but enhanced Th2 cell responses, suggesting that IL-23 secreted by DCs activated with anti-hDectin-1-HA1 could enhance Th1 and Th17 but suppress Th2 cell responses.

However, the findings by the present inventors also showed that this agonistic anti-hDectin-1 in recombinant fusion protein forms is not potent enough to abrogate Th2 cell responses. Therefore, the inventors studied the biological function of Dectin-1 agonists and toll-like receptor ligands below.

The human DCs activated via Dectin-1 result in enhanced Th1 and Th17 cell responses, but decreased Th2 cell responses. To study this the present inventors targeted Monocyte-derived IFNDCs with recombinant fusion proteins of anti-hDectin-1 fused to influenza HAL and co-cultured the with purified autologous CD4+ T cells in the presence or absence of Dectin-1 agonist. After one week, CD4+ T cells were restimulated with HA1-derived peptides for 36 h. Culture supernatants were analyzed for cytokines FIG. 2 shows that DCs activated with Dectin-1 agonists resulted in enhanced HA1-derived peptide epitope (pep7)-specific Th1 and Th17 cell responses. However, DC activation resulted in dramatically decreased pep7-specific Th2 cell responses. Lower panels in FIG. 2 summarize the data from 7 independent runs using cells from different healthy donors.

The inventors hypothesize that OX40L expressed on human DCs contributes to the Th2 cell responses. To study this the inventors measured the types of CD4+ T cell responses by restimulating CD4+ T cells with PMA and ionomycin (FIG. 3). As observed in antigen-specific CD4+ T cell responses (FIG. 2), CD4+ T cells co-cultured with DCs activated by Dectin-1 agonists resulted in enhanced Th1/Th17 cell responses, but decreased Th2 cell responses, as quantified by intracellular cytokine staining Right two panels in FIG. 3 are the summary of data from 9 independent runs using cells from different healthy donors.

Purified autologous CD4+ T cells were co-cultured with IFNDCs loaded with anti-hDectin-1-HA1 for 7 days in the presence of anti-OX40L or control antibody. CD4+ T cells were then restimulated with HA1-derived peptide epitopes for 36 h. FIG. 4A shows that blocking OX40L with anti-OX40L antibody resulted in decreased HA-specific Th2 cell responses. Total CD4+ T cells were restimulated and stained for intracellular IL-5 and IL-13 expression. The data in FIG. 4B is consistent with the data in FIG. 4A. Thus, it can be concluded that OX40L expressed on human DCs is a key factor to the enhanced antigen-specific and total Th2 cell response.

Dectin-1 agonists downregulate the OX40L expression on human DCs: Human IFNDCs were incubated for 48 h in the presence or absence of Dectin-1 agonists. Cells were stained for CD86 and OX40L (FIG. 5). DCs express OX40L on their surface after 24 h (upper panels in FIG. 5) and 48 h incubation (lower panels in FIG. 5). At both time points, Dectin-1 agonists down regulate the surface expression of OX40L. Right panels are the summary of data from four independent runs using cells from different healthy donors.

Dectin-1 agonists can downregulate OX40L expressed on TSLP-activated DCs: TSLP-mediated upregulation of OX40L has been strongly associated with Th2-mediated allergy and asthma. The inventors tested whether Dectin-1 agonists can down regulate OX40L expressed on TSLP-treated DCs (FIG. 6). Blood mDCs treated with TSLP express OX40L (left panel). Dectin-1 agonists can down regulate OX40L expression on the TSLP-activated mDCs in a dose dependent manner. Right panel summarize the data from three independent runs using cells from different healthy donors.

Both Dectin-1 agonists and TLR2 ligands abrogated the antigen-specific Th2 cell responses elicited by TSLP-activated blood mDCs. Blood mDCs pre-activated with TSLP were loaded with anti-hDectin-1-HA1 in the presence or absence of Dectin-1 agonists or TLR2 ligands. mDCs were co-cultured with purified autologous CD4+ T cells for 7 days. CD4+ T cell were restimulated with HA1-derived peptide epitopes for 36 h. Cytokine levels in the culture supernatants were measured. FIG. 7 shows that both Dectin-1 agonists and TLR2 ligands resulted in decreased Th2 cell responses. However, Dectin-1 agonists resulted in enhanced Th17 cell responses. Six independent runs using cells from different donors showed similar results (data not shown).

The present invention first demonstrates that healthy individuals maintain broad ranges of influenza-specific memory Th17 cells. Such memory Th17 cell responses are greatly enhanced by targeting antigens to DCs via hDectin-1 using recombinant proteins of agonistic anti-hDectin-1 fused to antigens plus TLR2 ligands. Considering the beneficial roles of memory Th17 cells in protective immunity to subsequent infections, data from this study will contribute to the design of vaccines against many infections. The anti-hDectin-1 mAb and influenza HA1 fusion protein also activates the DCs to secrete IL-23 that contributes to enhanced Th1/Th17 but decreases Th2 cell responses. It also down regulates TSLP mediated OX40L expression. This strategy is particularly useful in therapeutic applications against allergy, asthma or both.

It is contemplated that any embodiment discussed in this specification can be implemented with respect to any method, kit, reagent, or composition of the invention, and vice versa. Furthermore, compositions of the invention can be used to achieve methods of the invention.

It may be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it may be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

U.S. Patent Application Publication No. 2010/0166784: Method and Compositions For Modulating Th17 Cell Development.
U.S. Patent Application Publication No. 2008/0233140: Therapeutic Applications of Activation of Human Antigen-Presenting Cells through Dectin-1.

What is claimed is:

1. A method for treating allergy, asthma, or both in a subject having allergy, asthma, or both, the method comprising administering a Dectin-1 agonist and *P. gingivalis* LPS to the subject wherein the Dectin-1 agonist is an anti-Dectin-1-specific antibody or fragment thereof.

2. The method of claim 1, wherein the method is used in the treatment of a Th2-mediated allergy, asthma, or both.

3. The method of claim 1, wherein the Dectin-1 agonist decreases thymic stromal lymphopoietin (TSLP) mediated OX40 ligand expression.

4. The method of claim 1, wherein the Dectin-1 agonist is administered orally, parenterally, intranasally, by inhalation, mucosally, subcutaneously, intradermally, intravenously, and intramuscularly.

* * * * *

SEQUENCE LISTING

```
<160> NUMBER OF SEQ ID NOS: 8

<210> SEQ ID NO 1
<211> LENGTH: 24
<212> TYPE: DNA
<213> ORGANISM: artificial sequence
<220> FEATURE:
<223> OTHER INFORMATION: synthetic oligonucleotide

<400> SEQUENCE: 1
cactacagga tgtttgtgga cgtg                                          24

<210> SEQ ID NO 2
<211> LENGTH: 24
<212> TYPE: DNA
<213> ORGANISM: artificial sequence
<220> FEATURE:
<223> OTHER INFORMATION: synthetic oligonucleotide

<400> SEQUENCE: 2
ccccttgttg tttgtgagct ttag                                          24
```

```
<210> SEQ ID NO 3
<211> LENGTH: 24
<212> TYPE: DNA
<213> ORGANISM: artificial sequence
<220> FEATURE:
<223> OTHER INFORMATION: synthetic oligonucleotide

<400> SEQUENCE: 3
tctggagctg gcctttcatc atca                                          24

<210> SEQ ID NO 4
<211> LENGTH: 24
<212> TYPE: DNA
<213> ORGANISM: artificial sequence
<220> FEATURE:
<223> OTHER INFORMATION: synthetic oligonucleotide

<400> SEQUENCE: 4
tctgctcact tccaaagagc tggt                                          24

<210> SEQ ID NO 5
<211> LENGTH: 20
<212> TYPE: DNA
<213> ORGANISM: artificial sequence
<220> FEATURE:
<223> OTHER INFORMATION: synthetic oligonucleotide

<400> SEQUENCE: 5
aactgtgggg caacctcgac                                               20

<210> SEQ ID NO 6
<211> LENGTH: 20
<212> TYPE: DNA
<213> ORGANISM: artificial sequence
<220> FEATURE:
<223> OTHER INFORMATION: synthetic oligonucleotide

<400> SEQUENCE: 6
ttgcagacag ggtccccatt                                               20

<210> SEQ ID NO 7
<211> LENGTH: 20
<212> TYPE: DNA
<213> ORGANISM: artificial sequence
<220> FEATURE:
<223> OTHER INFORMATION: synthetic oligonucleotide

<400> SEQUENCE: 7
ggatgcagaa ggagatcact                                               20

<210> SEQ ID NO 8
<211> LENGTH: 20
<212> TYPE: DNA
<213> ORGANISM: artificial sequence
<220> FEATURE:
<223> OTHER INFORMATION: synthetic oligonucleotide

<400> SEQUENCE: 8
cgatccacac ggagtacttg                                               20
```